US006470279B1

(12) United States Patent
Samsoondar

(10) Patent No.: US 6,470,279 B1
(45) Date of Patent: Oct. 22, 2002

(54) METHOD FOR CALIBRATING SPECTROPHOTOMETRIC APPARATUS WITH SYNTHETIC FLUIDS TO MEASURE PLASMA AND SERUM ANALYTES

(76) Inventor: James Samsoondar, 40 Hilborn Avenue, Cambridge, Ontario (CA), N1T 1M7

( * ) Notice: Subject to any disclaimer, the term of this patent is extended or adjusted under 35 U.S.C. 154(b) by 0 days.

(21) Appl. No.: 09/447,215

(22) Filed: Nov. 23, 1999

(51) Int. Cl.$^7$ .......................... G06F 19/00; G01N 33/48
(52) U.S. Cl. ........................... 702/28; 356/42; 702/104
(58) Field of Search .................. 356/39, 40, 42; 702/22, 28, 85, 104, 30, 32

(56) References Cited

U.S. PATENT DOCUMENTS

| | | | |
|---|---|---|---|
| 4,866,644 A | | 9/1989 | Shenk et al. ............ 364/571.02 |
| 5,637,505 A | * | 6/1997 | Li et al. ........................ 436/11 |
| 5,846,492 A | * | 12/1998 | Jacobs et al. ................ 356/244 |
| 5,939,327 A | * | 8/1999 | Samsoondar ................. 436/164 |
| 6,013,528 A | * | 1/2000 | Jacobs et al. ................ 356/244 |
| 6,195,158 B1 | * | 2/2001 | Cadell et al. ................ 356/246 |
| 6,268,910 B1 | * | 7/2001 | Samsoondar et al. ......... 356/39 |
| 6,277,584 B1 | * | 8/2001 | Chu et al. ..................... 435/7.1 |
| 2001/0004285 A1 | * | 6/2001 | Cadell et al. ................. 356/39 |

FOREIGN PATENT DOCUMENTS

| | | | | |
|---|---|---|---|---|
| EP | 0 132 399 A | * | 1/1985 | .......... G01N/33/52 |
| WO | WO 94/08225 | | 4/1994 | |
| WO | WO 97/47972 | | 12/1997 | |

OTHER PUBLICATIONS

Heckman, et al., "Transfer of Near–Infrared Monochromator Calibrations for Tobacco Constituents to Tilting–Filter Instruments," Chimica Acta 192: 197–208 (1987).

Tietz Textbook of Clinical Chemistry, 2nd Ed. (1994), p. 2022–2025.

* cited by examiner

*Primary Examiner*—Patrick Assouad
(74) *Attorney, Agent, or Firm*—Katten Muchin Zavis Rosenman

(57) ABSTRACT

Described is a method for calibrating a spectrophotometric apparatus which is used to measure analytes in plasma and/or serum samples based on the calibration of a First Apparatus, and for recalibrating such apparatus, including recalibration of the First Apparatus all using synthetic calibrators. These apparatus use absorption of radiation to measure analytes in serum or plasma samples. The method described includes using synthetic calibrators which are submitted to the First Apparatus for measurement and compared with measurements of similar calibrators in a Second Apparatus and using the comparison to derive concentrations of analytes in samples measured on the Second Apparatus. As an alternative to making all apparatus identical, in terms of wavelength calibration, the absorbances of all apparatus should be mapped onto a standard set of wavelengths.

24 Claims, 9 Drawing Sheets

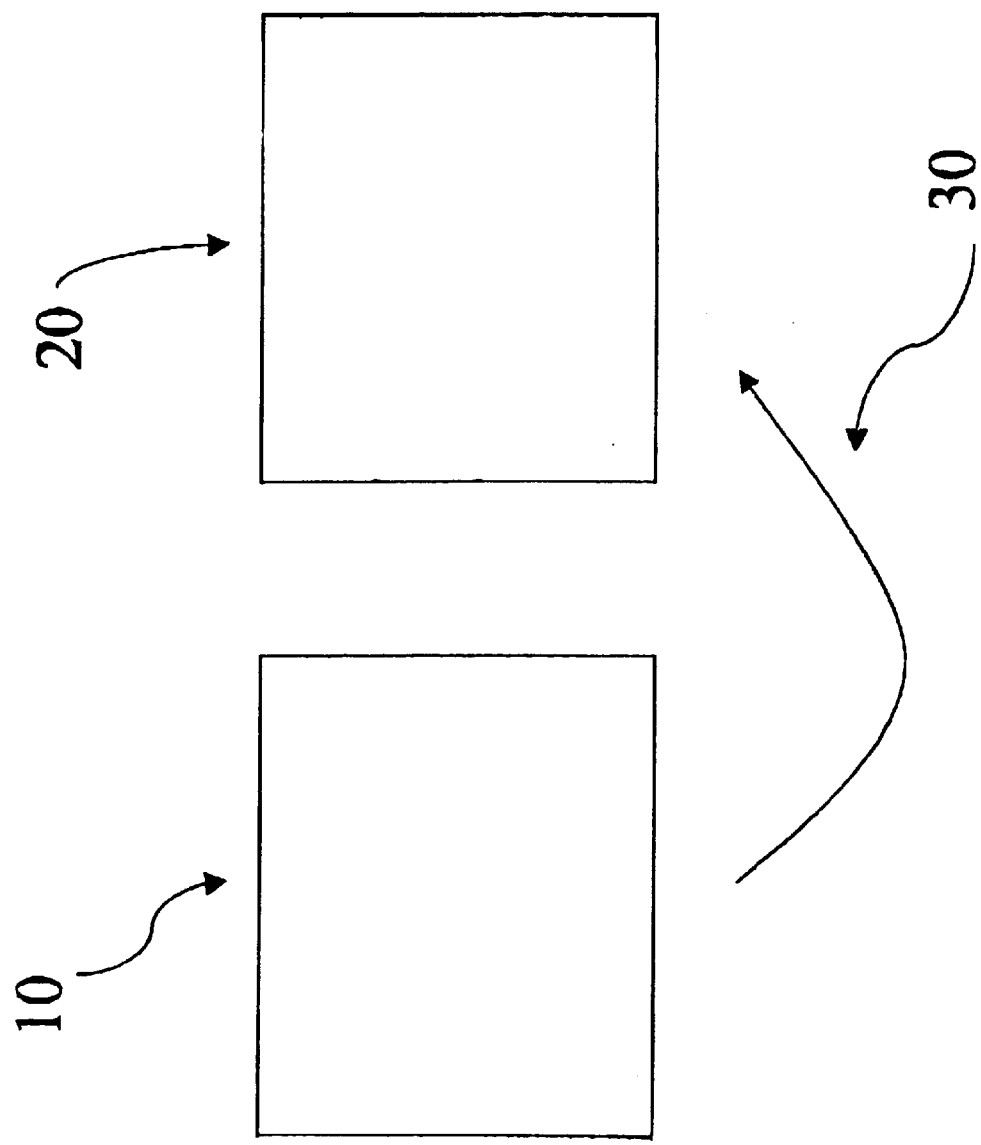

METHOD FOR CALIBRATING SPECTROPHOTOMETRIC APPARATUS WITH SYNTHETIC FLUIDS TO MEASURE PLASMA AND SERUM ANALYTES

FIELD OF INVENTION

This invention is in the field of spectrophotometric determinations of concentrations of substances in solution and relates to methods of calibration of apparatus used to measure quantity of one or more analytes or interferents in a serum or plasma specimen, using synthetic fluids.

BACKGROUND OF INVENTION

Clinical laboratory tests are routinely performed on serum or plasma of whole blood. In a routine assay, red blood cells are separated from plasma by centrifugation, or red blood cells and various plasma proteins are separated from serum by clotting prior to centrifugation. Hemoglobin (Hb), light-scattering substances like lipid particles, and bile pigments bilirubin (BR) and biliverdin (BV) are typical substances which will interfere with and affect spectrophotometric and other blood analytical measurements. Such substances are referred to as interferents, and they can be measured spectrophotometrically. The presence of such interferents affects the ability to perform tests on the serum or plasma and as such can be said to compromise specimen integrity. An apparatus or instrument used for measuring interferents in serum and plasma i.e., assess specimen integrity, is a substitute for visual inspection. The interferents may be regarded as analytes, with respect to the apparatus used to measure the interferents. Because quantitative results from the determination of the concentration of such interferents are reported based on specific calibration algorithms, there is a need to calibrate and to monitor calibration performance daily.

Unlike many blood analytical apparatus, calibration of spectrophotometric apparatus used to measure quantity of one or more analytes or interferents in a serum or plasma specimen is a cumbersome time intensive exercise (Primary Calibration). Each apparatus used for the purposes of determining the concentration of interferents must be calibrated according to this process and over the lifetime of an apparatus can amount to a considerable amount of time and cost. Accordingly, a faster, more cost effective method of calibration is desirable. An example of a method developed to address such problems using synthetic fluids follows: calibrators or synthetic fluids are tested on first instrument that is shown to be in control by quality control fluids. The absorbance measurements are saved. Primary Calibration Algorithms are applied to absorbance measurements made on first instrument, and predict analyte concentration(s). Concentrations of the analyte(s) predicted for calibrators, are stored on a calibration diskette. Install Primary Calibration Algorithms on second instrument.

Test calibrators on second instrument during calibration procedures. Apply Primary Calibration Algorithms to absorbance measurements made on second instrument, and predict analyte concentration(s). For each analyte, plot concentrations from first instrument on the x-axis, against concentrations from second instrument on y-axis, and obtain linear regression equation.

The linear regression equation for a particular analyte would be in the form, $y=mx+c$, where m is the slope and c is the y-intercept. All subsequent predictions by second instrument for the same analyte would be adjusted by subtracting "c" and dividing the difference by "m."

The major disadvantage with this method is that the calibrators need to be carefully designed to produce absorbance spectra that closely resemble the absorbance spectra of serum containing mixed or multiple interferents in the spectral section of the wavelengths used in the calibration algorithm. This can be accomplished through trial and error, but, the entire design and trial-and-error process must be repeated when new calibration algorithms use a different set of wavelengths. Also, such methods are only suitable when the calibration algorithms use a small number of wavelengths.

SUMMARY OF INVENTION

The present inventor has found that using synthetic fluids it is possible to rapidly and efficiently calibrate an apparatus and use the calibration algorithms of a First Apparatus which is conducted by the standard cumbersome time intensive exercise ("Primary Calibration") and a method for calibrating an apparatus based on the calibration of a First Apparatus, and for recalibrating such apparatus, including recalibration of the First Apparatus. According to one embodiment, these apparatus use absorption of radiation to measure analytes in serum or plasma samples. Throughout this application reference is made to measurements through absorption of radiation.

Accordingly, the present invention provides a method for transferring a calibration algorithm from a First Apparatus to a Second Apparatus whereby the Second Instrument need not be calibrated in the same way in which the First Apparatus was calibrated, i.e, by conducting a Primary Calibration.

According to one embodiment the present invention provides a method for transferring a calibration algorithm from a First Apparatus to a Second Apparatus comprising:

(i) conducting a Primary Calibration of the First Apparatus to obtain at least one Primary Calibration Algorithm using a standard set of wavelengths;

(ii) obtaining measurements of absorbance of a set of calibrators on the First Apparatus at the standard set of wavelengths (iii) obtaining calibration absorbance measurements of the set of calibrators on a Second Apparatus for at least one wavelength from the standard set of wavelengths;

(iv) establishing a First linear regression equation for each wavelength from the standard set of wavelengths using the calibration absorbance measurements from the First Apparatus and the Second Apparatus; and (v) incorporating the at least one Primary Calibration Algorithm on the Second Apparatus.

According to a method of the invention there is further provided a method of determining the concentration of an analyte in a sample in a Second Apparatus comprising:

(i) transferring a calibration algorithm from a First Apparatus according to the method just outlined above;

(ii) in the Second Apparatus measuring the absorbance of the sample at the standard set of wavelengths;

(iii) adjusting the measurements of absorbance from the sample with the First linear regression equation to obtain a corrected absorbance; and (iv) calculating a concentration for the analyte using the corrected absorbance. According to a preferred embodiment in the Primary Calibration Algorithms and the calibration absorbance measurements on the First Apparatus are electronically stored and installed on the Second Apparatus, more preferably on a floppy diskette or an EPROM.

According to another embodiment of the invention the samples used for the Primary Calibration are in a first type of vessel and the calibrators are in the same type of vessel, preferably a pipette tip, test tube (labelled or unlabelled), or blood bag tubing.

According to another embodiment of the method four calibrators are used, preferably all from the same batch, most preferably the calibrators mimic hemoglobin, bilirubin, turbidity or biliverdin.

According to another embodiment of the method the calibrators used in the Second Apparatus are exactly the same calibrators used to provide the absorbance measurement on the First Apparatus.

According to another embodiment of the method the standard wavelengths are measured in the near infrared and adjacent visible light spectrum, preferably ten absorbance measurements are taken at each wavelength of the standard wavelength set.

According to yet another embodiment, the method comprises conducting a Primary Calibration of a First Apparatus and using a quality control fluid to confirm the First Apparatus is functioning wherein the quality control fluid, or calibrator, is contained in a sample container. Next, two or more calibrators, called a "calibration set", are submitted to the First Apparatus and the absorbance for each of the calibrators is measured on the First Apparatus. These absorbance measurements are stored and provide "calibration absorbance measurements" from the First Apparatus for a calibration set. Also stored are the calibration algorithms from the First Apparatus. Preferably the calibration absorbance measurements and calibration algorithms from the First Apparatus is stored electronically, most preferably on a computer diskette. The calibration algorithms from the First Apparatus are installed in a Second Apparatus, preferably before the Second Apparatus is used. Using similar calibrators from the same batch, i.e., with identical lot number or batch number, which were measured on the First Apparatus and the same "standard set of wavelengths", the absorptions of the calibrators are measured on the Second Apparatus to generate a second set of measurements. These absorbance measurements from the Second Apparatus are also stored with the absorbance measurements from the First Apparatus. Next a first linear regression plot is prepared using the absorbances measured from each of the First and Second Apparatus for each wavelength. Measurements from the First Apparatus are plotted on one axis and measurements from the Second Apparatus are plotted on the second axis; preferably measurements from the First Instrument are plotted on the x-axis. The slope and intercept of this first linear regression plot are stored in the Second Apparatus. Using this stored regression data, the absorbances of actual samples which are measured on the Second Apparatus are adjusted using the stored regression plot for each wavelength. Accordingly, the measurement made in respect of the sample once adjusted, provides a result comparable to that which would be obtained if the sample had been measured on the First Apparatus. In this way, the Second Apparatus need not be calibrated through a Primary Calibration as was done for the First Apparatus.

Accordingly, the present invention provides a method of determining the concentration of an interferent in a sample in a Second Apparatus using a calibration algorithm from a First Apparatus comprising:

(i) conducting a Primary Calibration of the First Apparatus to obtain at least one Primary Calibration Algorithm using a standard set of wavelengths in the near infrared and adjacent visible range and storing the at least one Primary Calibration Algorithm on a floppy diskette;

(ii) obtaining calibration absorbance measurements of a set of four calibrators which mimic hemoglobin, bilirubin, turbidity or biliverdin on said First Apparatus at the standard set of wavelengths and storing the calibration absorbance measurements on the floppy diskette;

(iii) installing the calibration absorbance measurements and the at least one Primary Calibration Algorithms stored on the floppy diskette in the Second Apparatus;

(iv) obtaining measurements of absorbance of the set of calibrators on a Second Apparatus for at least one wavelength from the standard set of wavelengths;

(v) establishing a First linear regression equation for each wavelength from the standard set of wavelengths using the calibration absorbance measurements from the First Apparatus and the measurements of absorbance from the Second Apparatus and electronically storing the First linear regression equation in the Second Apparatus;

(vi) in the Second Apparatus measuring the absorbance of the sample at the standard set of wavelengths;

(vii) adjusting the measurements of absorbance from the sample with the First linear regression equation to obtain a corrected absorbance; and (viii) calculating a concentration for the interferent using the corrected absorbance.

As will be readily apparent to those skilled in the art, this set of measurements obtained from a First Apparatus, the "calibration absorbance measurements", may be applied to any Second Apparatus. Further, the same "calibration absorbance measurements" may be applied to the First Apparatus in order to recalibrate it. Accordingly, the present invention also provides a method for recalibrating an apparatus where the apparatus has the calibration algorithm from the First Apparatus installed. As is readily apparent, the calibration set may also be used to recalibrate any Second Apparatus so requiring recalibration.

According to an embodiment of this aspect of the invention, the calibrators are measured in the apparatus which is being recalibrated and absorbances recorded using the same standard set of wavelengths as used in the First Apparatus. New, or Second linear regression plot(s) is (are) then calculated for each wavelength with this set of calibration absorbance measurements versus the measurements obtained from the First Apparatus to generate a Second linear regression plot having an intercept and slope, which is then stored in the apparatus being recalibrated. Measurements of actual samples in the recalibrated apparatus are then adjusted using the Second linear regression plots.

Accordingly, the present invention provides a method for recalibrating a First Apparatus and/or a Second Apparatus comprising:

(i) incorporating in the First and/or Second Apparatus at least one Primary Calibration Algorithm and calibration of absorbance measurements of a set of calibrators at a standard set of wavelengths, obtained from a Primary Calibration on the First Apparatus;

(ii) obtaining measurements of absorbance of the set of calibrators on the First and/or Second Apparatus for at least one wavelength at the standard set of wavelengths; and (iii) establishing a Second linear regression equation using the incorporated calibration absorbance measurements and the measurements of absorbance obtained on the First and/or Second Apparatus.

As is readily apparent, any such apparatus which has been recalibrated may be used in a method according to the present invention to determine the concentration of an analyte in a sample in an apparatus by steps comprising:

(i) measuring the absorbance of the sample in the recalibrated apparatus at the standard set of wavelengths;

(ii) adjusting the measurements of absorbance from the sample with the Second linear regression equation to obtain a corrected absorbance; and (iii) calculating a concentration for the analyte using the corrected absorbance. According to a preferred embodiment the samples used for the Primary Calibration are in a first type of vessel and the calibrators are in the same type of vessel, preferably a pipette tip, test tube (labelled or unlabelled), or blood bag tubing.

According to one embodiment of the method of recalibration four calibrators are used, preferably all from the same batch and the calibrators mimic hemoglobin, bilirubin, turbidity or biliverdin.

According to another embodiment of the method the standard wavelengths are measured in the near infrared and adjacent visible light spectrum, preferably ten absorbance measurements are taken at each wavelength of the standard wavelength set.

As stated above, the calibrators used in the methods of the present invention are substances each of which may mimic a constituent in the sample which is being measured by the apparatus, although it is not necessary that they mimic a constituent in the sample.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 9 shows the relationship between a First Apparatus and a Second Apparatus as described herein.

DETAILED DESCRIPTION OF INVENTION

Figure 1:
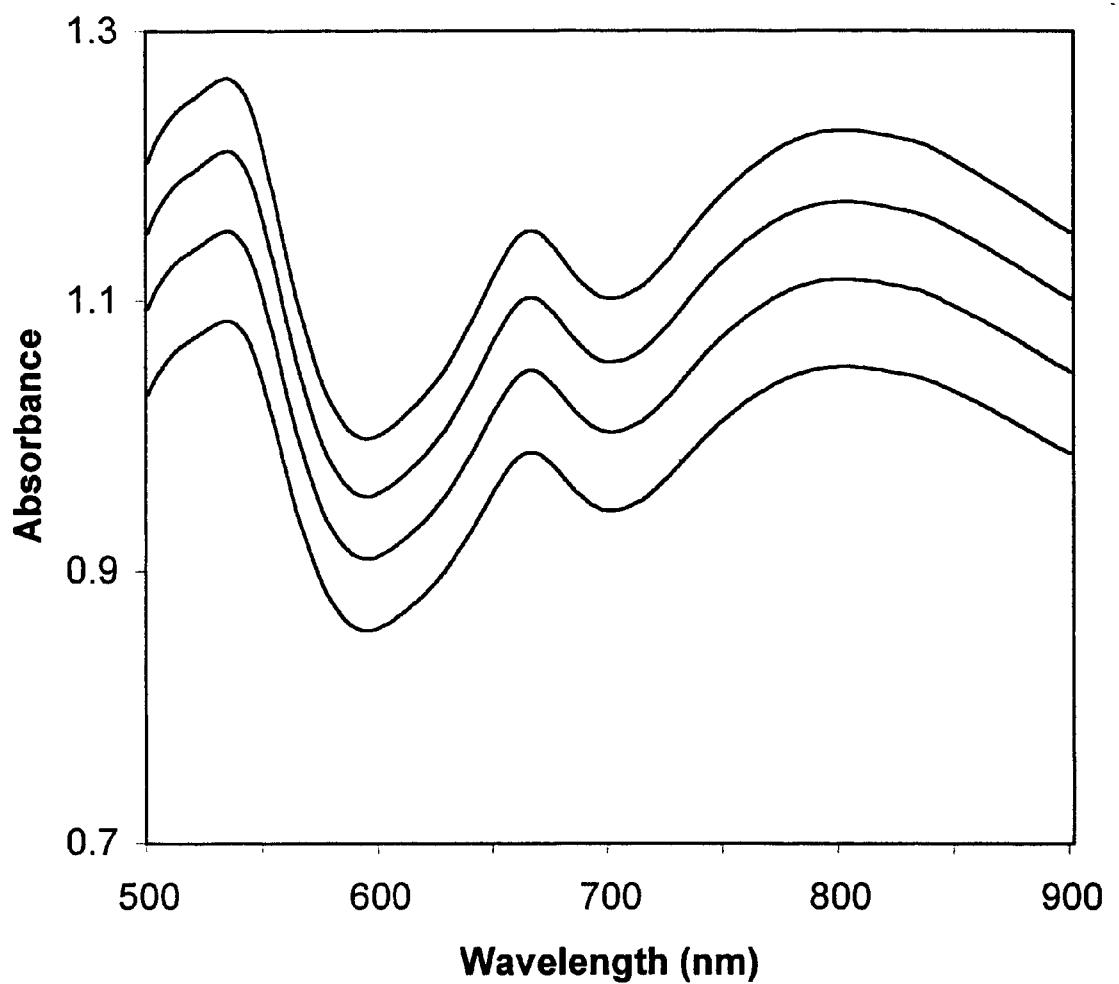
FIG. 1 is a graphic representation of the absorbance spectra of four different synthetic calibrators, tested on the First Apparatus.

As mentioned above the present invention provides a method for calibrating an apparatus based on the calibration of a First Apparatus, and for recalibrating such apparatus, including recalibration of the First Apparatus. According to one embodiment, these apparatus use absorption of radiation to measure analytes in serum or plasma samples. Throughout this application reference is made to measurements through absorption of radiation. While this is preferred it should be understood that the present invention is not limited to absorption and measurements by other means such as reflectance are also within the scope of the present invention.

According to a preferred embodiment, these apparatus are used to measure concentrations of interferents using radiation, most preferably using near infrared radiation and the adjacent visible radiation spectrum.

As used herein the following terms have the following meaning: "analytes" means a substance contained in blood, serum and/or plasma. "Interferents" means an analyte whose presence in a specimen interfers with the determination of the presence and/or quantification of an analyte. "Primary Calibration Algorithm" is the algorithm obtained from the Primary Calibration of a First apparatus. Two or more calibrators provides a "calibration set" as referred to herein. "Discrete wavelength" concerns the simplest calibration algorithm required and requires the absorbance at a single wavelength, e.g., for simple linear regression. Several discrete wavelengths could be used for more complex calibration algorithms, for example for multiple linear regression. "Section or sections of spectrums" means absorbance at more than one wavelength where the wavelengths are in succession. "Full spectrum" concerns the most complex calibration algorithms, and relates to the absorbances at different continuous sections of the absorbance spectrum, up to and including the complete spectrum, which would be required for the algorithm, e.g., for Partial Least Squares ("PLS") analysis. Sections of the spectrum can be used for PLS analysis. "Vessels" includes translucent containers and can be anything which is translucent and capable of holding a sample, preferably fluid, to enable measurement of absorbance and/or reflectance of radiation in the sample. Examples of vessels include, pipette tips, tubing, cuvettes, test tubes (with and without labels), blood bag tubing, and any other translucent vessel. "Standard set of wavelengths" is a wavelength table used by all apparatus. The actual set of wavelengths provided by an apparatus depends on the manner in which the wavelength calibration was performed. It is desirable that each apparatus should provide the same set of actual wavelengths, but this is not necessary. As an alternative, the absorbances corresponding to the actual wavelengths of the apparatus can be mapped onto a "standard set of wavelengths," thereby allowing the different apparatus the appearance of having been provided the same set of actual wavelengths.

Primary Calibration—Preparation of Calibration and Validation Sets

As stated above, Primary Calibration of an apparatus is a cumbersome time intensive exercise. Each apparatus used for the purposes of determining the concentration of interferents or blood analytes, must be calibrated according to this process on an as needed basis. The Primary Calibration procedure, in respect of interferents, is set out here. Although it will be appreciated by those skilled in the art that the procedures set out here for interferents will apply to any analyte, in any biological or non-biological fluid.

A Primary Calibration Algorithms developed as a result of the Primary Calibration will be installed in all other, or second apparatus. This installation can take place at any time, including when the second apparatus is being manufactured. According to a preferred embodiment, and with reference to FIG. 9, the Primary Calibration Algorithms prepared on a First Apparatus (10) are incorporated into an EPROM which is installed (30) in a Second Apparatus (20). According to another preferred embodiment, the Primary Calibration Algorithms are stored on a calibration diskette (discussed further below). The transferred algorithms (30) can only be used after the other apparatus have their absorbances measured in respect of the same standard set of wavelengths used for the Primary Calibration. Absorbances at each wavelength should undergo "photometric corrections" using the fluids. The photometric correction is the basis for the calibration process. Examples of slopes and intercepts which may be used for photometric corrections are given in Table 1.

Hemoglobin

To prepare a Primary Calibration Algorithm for hemoglobin, sixty serum specimens with no visible interferents were stored refrigerated or frozen until used. More less specimens may be used so long as a sufficient number is used to provide a reliable result. Hb, Intralipid™ (IL), BR and BV were added to the normal sera to give final concentrations of 0–6.1 g/L, 0–5.1 g/l, 0–42.7 mg/dL, and 0–4.4 mg/dL respectively. The stock Hb was prepared by replacing the plasma (must be free from all interferents) from a blood sample, with twice its volume of water, and lysing the cells through three freeze-thaw cycles. For each cycle the blood was left in the freezer for 45–60 minutes, and then removed and placed on a rocker at room temperature for 30–45 minutes. Hb content of the lysate was measured by the reference method described below, after removing the red blood cell (RBC) debris and unlysed RBC's by centrifuging at 10,000 ×g for 10 minutes. Although any method which provides a reliable determination of content may be used. A typical hemolysate contains approximately 100 g/L Hb. CO-oximetry suggests that more than 95% of the Hb is in the oxy-state. The stock BV was prepared by dissolving biliverdin dihydrochloride (from Sigma) initially in 50% methanol-50% water, and diluting further with phosphate buffered saline (PBS). The stock IL also known as Travamulsion™ (from Clintec-Nestle & Baxter), has a concentration of 10%. The stock BR was prepared by dissolving Ditauro-Bilirubin (from Porphyrin Products, Logan, Utah, USA) in interferent-free serum, to a concentration of 500 mg/dL. In order to make the Ditauro-Bilirubin equivalent to the BR contained in patient sera, the stock concentration was divided by 1.23. The spectral absorbance data were recorded for the 60 samples using different polypropylene dispensing tips. Out of the 60 samples, the odd numbers were used for the calibration set, and the even numbers were used as the validation set.

Bilirubin

The sample set used for Hb and BV calibrations cannot be used for BR calibration, because the absorbance due to either Hb>4g/L or IL>4g/L, approaches the limit of the apparatus in the region around 524 nm, the primary wavelength used for BR calibration. Instead, a separate set of 60 samples were prepared and tested. As will be readily appreciated by those skilled in the art, the sample set used for Primary Calibration should be of a size sufficient to include most of the variability encountered with actual patient sample(s), such as serum or plasma. The samples were prepared as before by adding Hb, IL BR and BV to the normal sera to give final concentrations of 0–2.6 g/L, 0–3.6 g/l, 0–37 mg/dL, and 0–4.4 mg/dL respectively. The spectral absorbance data were recorded for the 60 samples using different polypropylene dispensing tips. Out of the 60 samples, the odd numbers were used for the calibration set, and the even numbers were used as the validation set. The stock interferents were prepared as described above for Hb, and the BR concentrations were adjusted by the factor 1.23. The 1.23 factor that was derived previously from the slope of the regression line obtained from a validation set using real icteric serum and plasma samples.

Turbidity

Turbidity in serum and plasma is caused mainly by the presence of fat particles, particularly chylomicrons. Intralipid (IL) is a fat emulsion which mimics naturally-occurring chylomicrons, and therefore may preferably be used to simulate turbidity in serum and plasma.

Samples used for Hb and BR calibration are preferably not used for IL calibration because the Hb stock solution contributes significant light scattering due to unlysed RBC's and RBC fragments. Centrifugation of the hemolysate was unable to remove all the unlysed RBC and RBC fragments.

Forty samples of PBS (phosphate buffered saline) were spiked with 10% Intralipid to produce concentrations of 0–20 g/L. The spectral absorbance data were recorded for the 40 samples using different polypropylene dispensing tips. Out of the 40 samples, the odd numbers were used for the calibration set, and the even numbers were used as the validation set.

As mentioned above, the Primary Calibration described herein is exemplary of the work involved in developing Primary Calibration Algorithms. Other analytes may be used to develop such Primary Calibration Algorithms.

Reference Methods

The sample absorbance data and the concentrations of the interferents are required for development of calibration algorithms for the interferents. Any errors in the reference methods used to measure the concentration of the interferents will affect the performance accuracy of the calibration algorithms.

Hemoglobin

For validation using spiked serum samples, the Hb concentration in the hemolysate was used to calculate the reference Hb values. For validation using serum or plasma samples, methods known to those skilled in the art, such as for example: Tietz Textbook of Clinical Chemistry, 1994, page 2024, may be used; the same method is used to determine the Hb concentration in the hemolysate.

For accurate hemoglobin measurement in serum and plasma samples, preferably they will be the only interferent present, and the absorbances at 578 nm, 562 nm, and 598 nm are measured.

$$\text{mg/dL Oxyhemoglobin} = 155.0\, A_{578} - 86.1 A_{562} - 68.9 A_{598}$$

where A is the absorbance at the wavelengths specified in nanometers. Appropriate dilutions are performed to produce absorbances between 1.0 and 2.0, for the 578 nm wavelength.

As appropriate, dilutions may be made with 10 mg/dL sodium carbonate. Stock sodium carbonate which is stable at room temperature for up to 1 year, may be made by dissolving 1 g of sodium carbonate in 100 mL distilled water. Working solution of sodium carbonate, which is also stable at room temperature for up to 1 year, may be made by diluting 1 mL of stock solution to 100 mL with distilled water.

For the present illustration of Primary Calibration, a Shimadzu single-beam scanning spectrometer with a grating was used, although any comparable apparatus may be used. This spectrophotometer has a 2-mm spectral bandpass and covers the wavelength range of 190–1100 nm. Since there is no commercial calibrator for oxyhemoglobin, the spectrophotometer used is preferably checked for wavelength and absorbance (or photometric) accuracy.

Bilirubin

For validation using spiked serum samples, the concentration of synthetic ditauro bilirubin added, divided by 1.23, was used as the reference total BR value. For validation using patient serum or plasma samples, any total bilirubin test performed by chemistry analyzers (e.g., Beckman-Coulter or Ortho-Clinical Diagnostics general chemistry analyzers) used by accredited medical laboratories could be used as the reference method.

Turbidity

For validation using PBS spiked with IL, the concentration of the IL present was used as the reference value. In Tietz Textbook of Clinical Chemistry, 1994, page 2022, absorbance measurement at 700 nm is used to make corrections for turbidity. Therefore, for this instance, validation using patient serum or plasma samples, absolute absorbance at 700 nm will be adopted as the reference method. A commercial single beam spectrophotometer should be used with a 10 mm×10 mm cuvette, referenced against PBS. The absorbances before or after dilutions are preferably between 0.2 and 2.0. Photometric and wavelength accuracy of the reference spectrophotometer is preferably demonstrated.

Primary Calibration Algorithms

The following Primary Calibration Algorithms were developed for Hb, BR and IL (turbidity) in disposable polypropylene dispensing tips using the Primary Calibration approach set forth above.

Hemoglobin $$\text{g/L Hb} = 16.81(1\text{st}D\,A584) - 79.47(1\text{st}D\,A599) + 60.95(1\text{st}\,D\,A617) + 0.24$$

where (1st D A) is the first derivative of the absorbance measurement at the wavelength specified in nanometers.

Bilirubin $$\text{mg/dL BR} = -293.1(1\text{st}\,D\,A524) - 327.8(1\text{st}\,D\,A587) + 451.7(1\text{st}\,D\,A602) - 7.5$$

where (1st D A) is the first derivative of the absorbance measurement at the wavelength specified in nanometers.

Turbidity

Turbidity is measured in terms of equivalent IL concentration.

$$\ln(\text{g/L IL}) = 1.867(A700) - 0.447(A700)^2 + 0.041(A700)^3 - 1.33$$

where (A) is the raw absorbance measurement at the wavelength specified in nanometers.

A further set of Primary Calibration Algorithms developed on another apparatus used to test the samples for measurement in translucent pipette tips, and are as follows:

Hemolysis $$(\text{g/L})\text{Hb} = 30.14(1\text{st}\,D\,A591\text{ nm}) - 27.98(1\text{st}\,D\,A610\text{ nm})$$

where (1st D A) is the first derivative of the absorbance measurement at the wavelength specified.

Turbidity $$\text{g/L IL} = 296.01(A900\text{ nm}) - 0.04$$

where (A) is the raw absorbance measurement at the wavelength specified.

Bilirubin $$\text{mg/dL BR} = 142.09(1\text{st}\,D\,A511\text{ nm}) + 89.9(1\text{st}\,D\,A554\text{ nm}) - 4.47$$

where (1st D A) is the first derivative of the absorbance measurement at the wavelength specified.

Biliverdin $$\text{mg/dL BV} = 160.29(1\text{st}\,D\,A718\text{ nm}) - 206.15(1\text{st}\,D\,A781\text{ nm}) + 1.42$$

where (1st D A) is the first derivative of the absorbance measurement at the wavelength specified.

The Primary Calibration Algorithms referred to herein are non-limiting examples obtained by a process of multiple linear regression. The calibration process described using synthetic fluids is preferred because it produces more accurate results, and can be used regardless of the number of wavelengths used in the calibration algorithms. Therefore in addition to being suitable for multiple linear regression, it can also be used when methods like Partial Least Squares (PLS) are use to develop calibration algorithms. PLS uses all the wavelengths in the spectrum or sections of spectrum specified. Also, the calibration process described is the same for any calibration algorithm, making it suitable for measuring other substances in serum, plasma, or any other fluid in any type of translucent container or vessel.

Some reasons why different calibration algorithms are generated are as follows: The calibration algorithms are generated by different people, using the same software tools; The calibration algorithms are generated by the same or different people, using different software tools; Wider analytical range is required (e.g., measuring high levels of Hb-based blood substitutes, which appear as high levels of real Hb). The conventional method to deal with a concentration which exceeds the upper limit of the analytical range, is to dilute the sample. In this invention, new wavelengths can be used, and/or new mathematical transformation(s) can be used, instead of diluting the sample; for example, look at the two different IL calibration algorithms (one is cubic and uses natural logs; the other uses a single term and is linear); greater accuracy is required at low concentrations of interferents. E.g., a calibration algorithm can be developed to measure traces of Hb in serum or plasma, for a small analytical range—when the predicted value exceeds the upper limit of the small analytical range, the software will be prompted to use a different calibration algorithm; and finally when the wavelength range provided by the apparatus is limited. For example, one apparatus may only have the capability of measuring 450–750 nm, instead of 450–1100 nm. E.g., look at the two different IL calibration algorithms above (one uses 900 nm and one uses 700 nm).

Different Primary Calibration Algorithms should be developed for calibrator(s) in any one type of container, including, for example, tube, pipette tip, or similar translucent material. Also algorithms may be developed for several different types of tubes combined or different translucent materials combined. As is clear from the above discussion the calibrator(s) measurements in a First Apparatus will be conducted with the calibrator in a container. According to a preferred embodiment of the method of the invention, measurements of the calibrator in a Second Apparatus (20, FIG. 9) are conducted with the calibrator in the same type of container as used in the First Apparatus (10, FIG. 9). A further aspect of consideration with respect to calibrators is that the calibrator used for measurements in the First Apparatus and the Second Apparatus be from the same batch. In a preferred embodiment, a large batch of calibrators is prepared so that there will be a significant period of time before the batch expires or is depleted. In any event, at some time a new batch of calibrators will be required and that time it is preferable that a further Primary Calibration be conducted. This Primary Calibration may be conducted on the same First Apparatus as used in respect of the first batch of calibrators or a different First Apparatus may be used. In addition, different calibrators may be chosen and the batch may therefore include different calibrators. Once the new batch of calibrators is chosen and prepared, the Primary Calibration as described above is conducted in respect of the First Apparatus and as described above, absorbance measurements of the calibrators are taken, and this information is provided in the calibration information package which will be used for subsequent calibrations and recalibrations of apparatus. In the alternative, rather than conducting new Primary Calibration of a new First Apparatus, where a First Instrument is in control the Primary Calibration Algorithms contained in the First Apparatus which is in control should be satisfactory and the apparatus should be used to generate absorbance measurements in respect of the new batch of calibrators. This new set of Primary Calibration Algorithms and absorbance measurements in respect of the new batch of calibrators. This new set of Primary Calibration Algorithms and absorbance measurements from the new batch of calibrators are incorporated into a calibration information package (30, FIG. 9). In this circumstance or in the circumstances where new Primary Calibration Algorithms are generated on the basis of a new Primary Calibration of a First Apparatus (10, FIG. 9), a software within the Second Apparatus (20, FIG. 9) is receiving the calibration information package should be able to determine whether a new Primary Calibration Algorithm and a new First Apparatus was used in generating the calibration information package and absorbance measurements. In such cases, preferably, the Second Apparatus will automatically incorporate the "new" Primary Calibration Algorithms and absorbances from the calibration package.

Preparation of Calibration Information Package

Software may be designed to prepare Calibration Information packages or Calibration packages, although any other means by which the Primary Calibration Algorithms and absorbance information may be transferred are within the scope of the present invention. In one embodiment of the invention, the Calibration package is stored on a diskette although any other means of information transfer is contemplated, including CD-ROM, e-mail, internet information packages. These approaches will carry the calibration set (30, FIG. 9) from the "First Apparatus" (10, FIG. 9) to the "Second Apparatus" (20, FIG. 9). Preferably, Calibration packages should accompany calibrators, to enable users to recalibrate other apparatus when necessary, with minimum effort.

A Calibration package will most preferably contain the following pieces of information: the serial number of the first apparatus (i.e., the apparatus used to develop the Primary Calibration Algorithms); the calibration algorithms developed on the First apparatus; the vessel used as sample container and used for testing the calibrators on "first apparatus" must be checked from a list of sample containers e.g., tips, tubes, tubing; the lot number of the synthetic calibrators; the absorbance data for each calibrator, at all the wavelengths available on the "first apparatus". In a preferred embodiment, the calibrators may be tested as a patient sample, but unlike a patient sample, an average of measurements may be used, instead of a single measurement. According to one embodiment of the method of invention, the calibrators are multi-constituent calibrators, although some may not be used for all the interferents for which the "first apparatus" is calibrated. Therefore the Calibration package should indicate the interferents for which each calibrator can be applied.

Software tools used for preparing Primary Calibration Algorithms include the following: Mathlab™ used to create programs for "smoothing" absorbance data. MS Excel™ may be used to develop macros for calculating first derivative of absorbances; StatView™ used to create algorithms by a process called "step-wise multiple linear regression." Measurements for all the wavelengths can be presented to the StatView™ program, and only the significant wavelengths would be selected for the algorithms. Further, wavelengths which contribute least to the algorithms, can be eliminated until the desired number of wavelengths are left; and Pirouette™ which is used to create calibration algorithms by Partial Least Squares or Principal Component Analysis, using the measurements for all the wavelengths, or selected sections of the absorbance spectra.

Calibrators

Calibrators used in the method of the invention are substances which mimic the constituent of the sample which is subject to measurement in an apparatus. In respect of spectrophotometry of laboratory samples such as plasma or serum, calibrators, which are synthetic fluids, will mimic constituents such as hemoglobin, turbidity, bilirubin and biliverdin. Where hemoglobin is the constituent to be mimicked by a calibration material, substances which may be used include amaranth, phenol red and basic fusion. Examples of such calibrators are discussed here and in WO 97/47972 entitled "Calibrator Material For Instruments Which Measure Interferents in Serum and Plasma Specimens." Where the substance to be mimicked is turbidity, it can be selected from a group including titanium dioxide, copper sulfate and Intralipid™. Where the substance is bilirubin, calibration materials include methyl orange, amaranth and phenol red. Where the substance is biliverdin, the calibration material can be methylene blue, azure, thionine and toluidine blue O.

The use of such calibrators is preferred to Primary Calibration because of the following: a much smaller number of synthetic calibrators is required; synthetic calibrators are ready to use—materials for a Primary Calibration may not always be so readily available and cannot be stored for more than one day; synthetic calibrators are stable at room temperature and have a long shelf life. The materials used in a Primary Calibration do not have either of these attributes. Primary Calibration Algorithms require a skilled user, and are usually developed off-line. Finally, with carefully designed software, synthetic calibrators are relatively easy to use.

A composition of calibrators is preferably prepared in a buffered solution, preferably saline and more preferably phosphate buffered saline with the pH adjusted to about 7.4. For the method of this invention a lipid emulsion of any source commercially available, e.g., IL, can be used. As just stated, methylene blue can be used in place of biliverdin dihydrochloride; in this case 10 millimoles per liter sodium bicarbonate should be used instead of the phosphate buffered saline. For stability, the calibrator material can be sterilized by autoclaving and/or by addition of preservatives. As mentioned, a variety of dyes may be used, for example, phenol red or basic fuchsin may be used to mimic hemoglobin; phenol red at acidic pH's or amaranth at slightly higher pH may be used to mimic bilirubin; azure, thionine, or toluidine blue O may be used in combination with amaranth, to mimic biliverdin. In respect of alternatives to mimic turbidity, any substance which produces an absorbance pattern similar to the "apparent" absorbance in the region used by a calibration algorithm, may be used. One such example is copper sulfate. Turbidity causes an increase in the "apparent" absorbance. Apparent absorbance is based on the fact that transmitted light is measured and converted to absorbance units, therefore an apparatus cannot distinguish true absorbance from loss of light due to scattering. In some cases, turbidity produces absorbance which is inversely proportional to wavelength. Turbidity is monitored by absorbance at 700 nm or 900 nm, but could also be monitored by the slope of the absorbance curve at a single wavelength, namely, in the region greater than 800 nm.

A calibrator can include more than one component, for example by combining different amounts of stock solutions of amaranth, phenol red, copper sulfate, and toluidine blue O, dissolved in 100 millimoles per liter acetate buffer with pH values between 3 and 4. The concentration of a stock solution will only serve as a guide to the amount of the stock which should be added to make a lot of calibrator material.

A preferred formulation of calibrators is a combination of amaranth, phenol red, copper sulfate, and toluidine blue O, in 100 millimoles per liter acetate buffer, pH 3 to 4.

"Calibration" of Second Apparatus

The Primary Calibration Algorithms from the First Apparatus are installed in Second Apparatus, referred to as a "Second Apparatus." Because the "Second Apparatus" are not identical to the "First Apparatus," it is expected that certain adjustments must be made to the Primary Calibration Algorithms. As stated above, a first step in the method is to develop a standard set of wavelengths which all apparatus must use. The absorbance values for the standard set of wavelengths can be obtained from the measured absorbances at the apparatus-specific wavelengths, by interpolation of absorbances at wavelengths adjacent to the standard wavelengths.

For example, four calibrators are used. The absorbances at each of the standard wavelengths of the standard set of wavelengths is taken as the mean of measurements on the "First Apparatus". As will be readily appreciated, the number of measurements taken per wavelength can vary depending on the precision of the "First Apparatus." Further, smoothing of these measurements may be performed by techniques known to those skilled in the art. For the purposes of the method of the invention, if any smoothing is conducted in the First Apparatus, the same smoothing is applied to the measurements from a Second Apparatus. A linear regression equation is established for each wavelength using the stored absorbances obtained from the "First Apparatus" plotted on the x-axis, and the absorbance measured on the "Second Apparatus" plotted on the y-axis. The measurements on the "Second Apparatus" can be a single measurement or average of multiple measurements depending on the precision of the "Second Apparatus," and the desirable ease of recalibration. Each absorbance measurement on the "Second Apparatus" must be adjusted by dividing the difference between the measured absorbance and the y-intercept of the regression equation, by the slope of the regression equation. The absorbance adjustment using the calibrators have proven to be sufficient to complete the algorithm transfer from the "First" to "Second" apparatus.

Recalibration

When QC predictions by any apparatus are unacceptably far from assigned target values for any one interferent, the synthetic calibrators must be re-tested on that particular apparatus to generate a new set of slopes and intercepts. Some reasons why QC's fail are as follows: Lamp output is decreasing as lamp ages; Lamp burns out and has to be replaced; An optical fiber is damaged and has to be replaced; A diode array detector has to be replaced; When specimens are contained in different vessels (e.g., dispensing tips, tubes or blood bag tubings) from the type of vessel actually used to develop primary algorithms. As discussed above, the calibration package that accompanies the calibrators will be specific for the sample container or vessel. The calibrator diskettes will contain absorbance data generated by testing the calibrators in the appropriate vessel. Recalibration will most preferably be conducted when the quality controls do not produce results close enough to their established target values.

The following non-limiting examples are illustrative of the invention:

EXAMPLES

Figure 2:
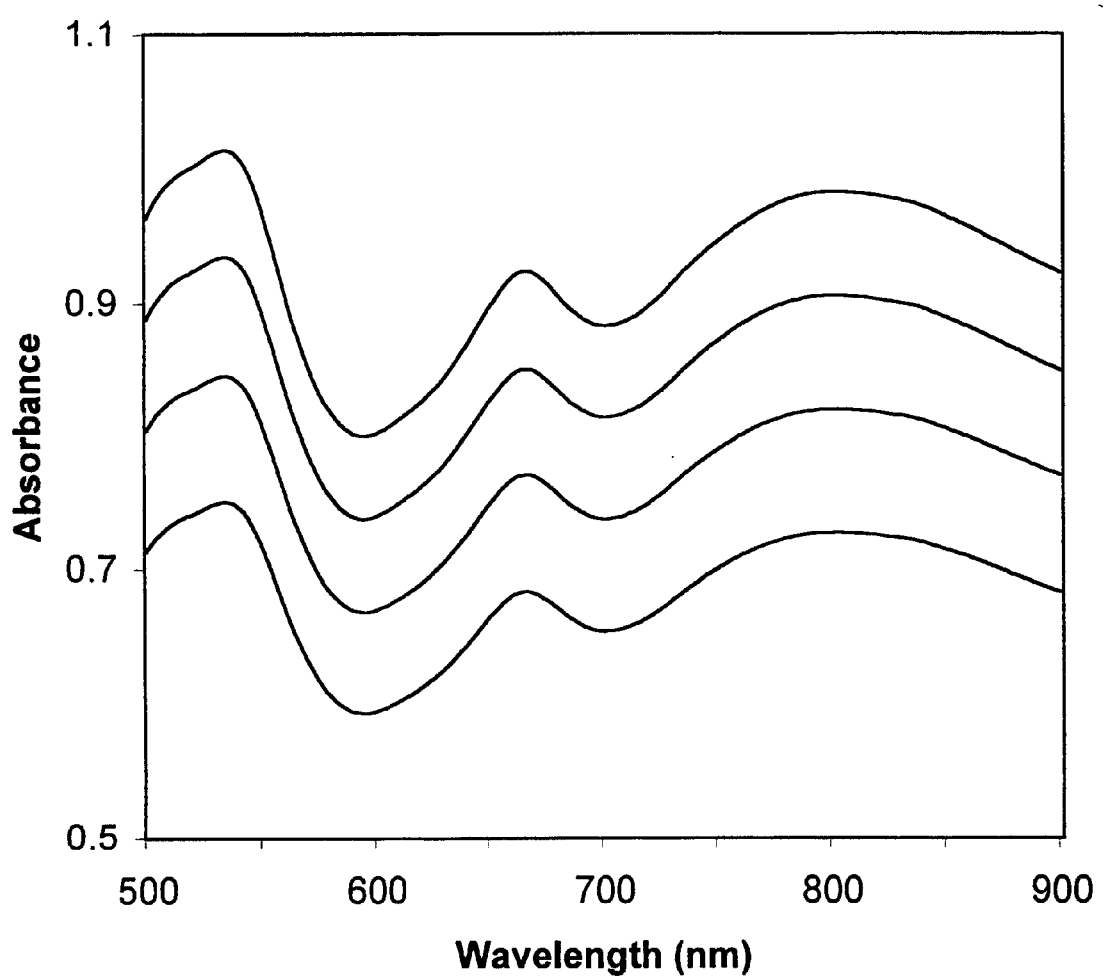
FIG. 2 is a graphic representation of the absorbance spectra of four different synthetic calibrators, tested on the Second Apparatus.
Figure 3:
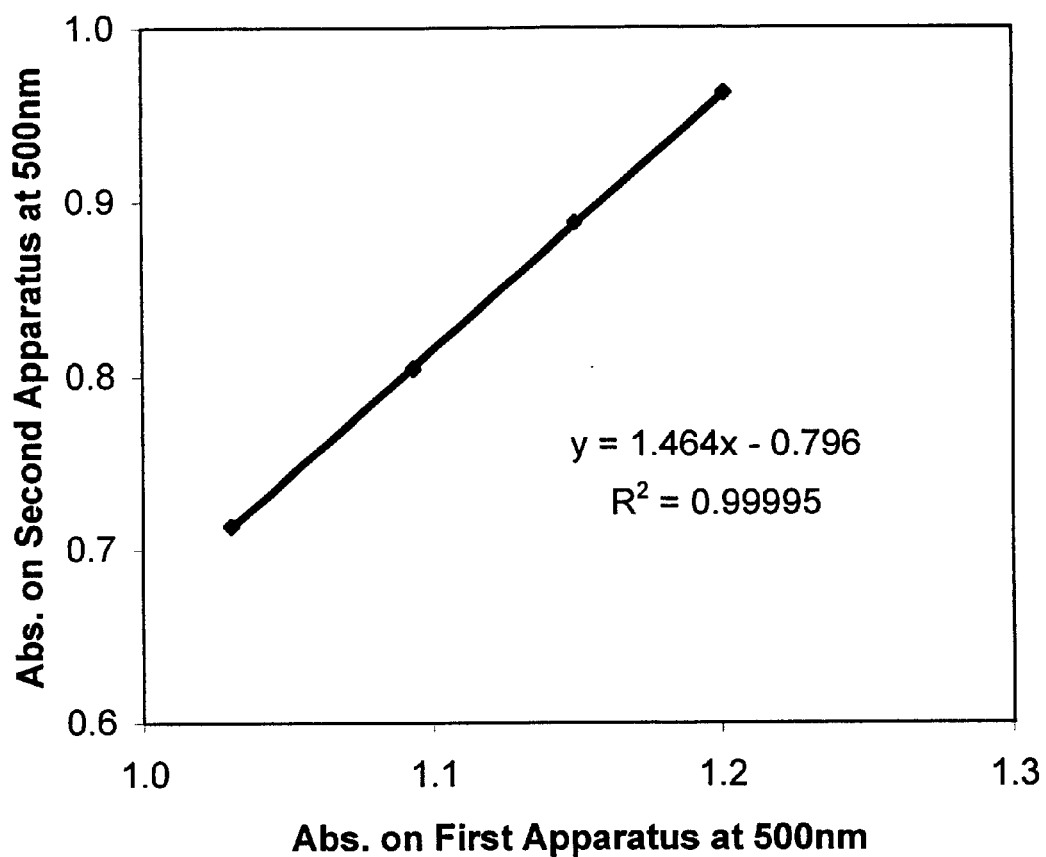
FIG. 3 is scatter plot of the absorbances of the four calibrators at 500 nm, when tested on the First Apparatus (x-axis) and the Second Apparatus (y-axis)
Figure 4:
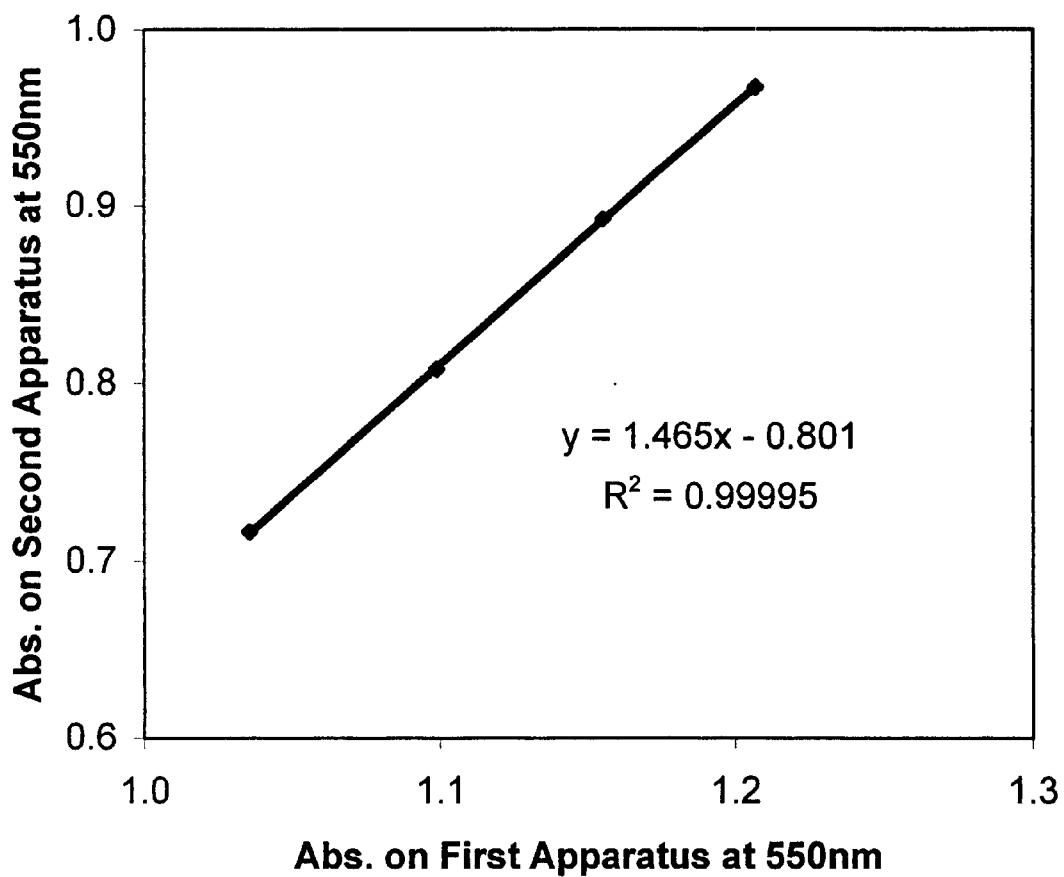
FIG. 4 is scatter plot of the absorbances of the four calibrators at 550 nm, when tested on the First Apparatus (x-axis) and the Second Apparatus (y-axis)
Figure 5:
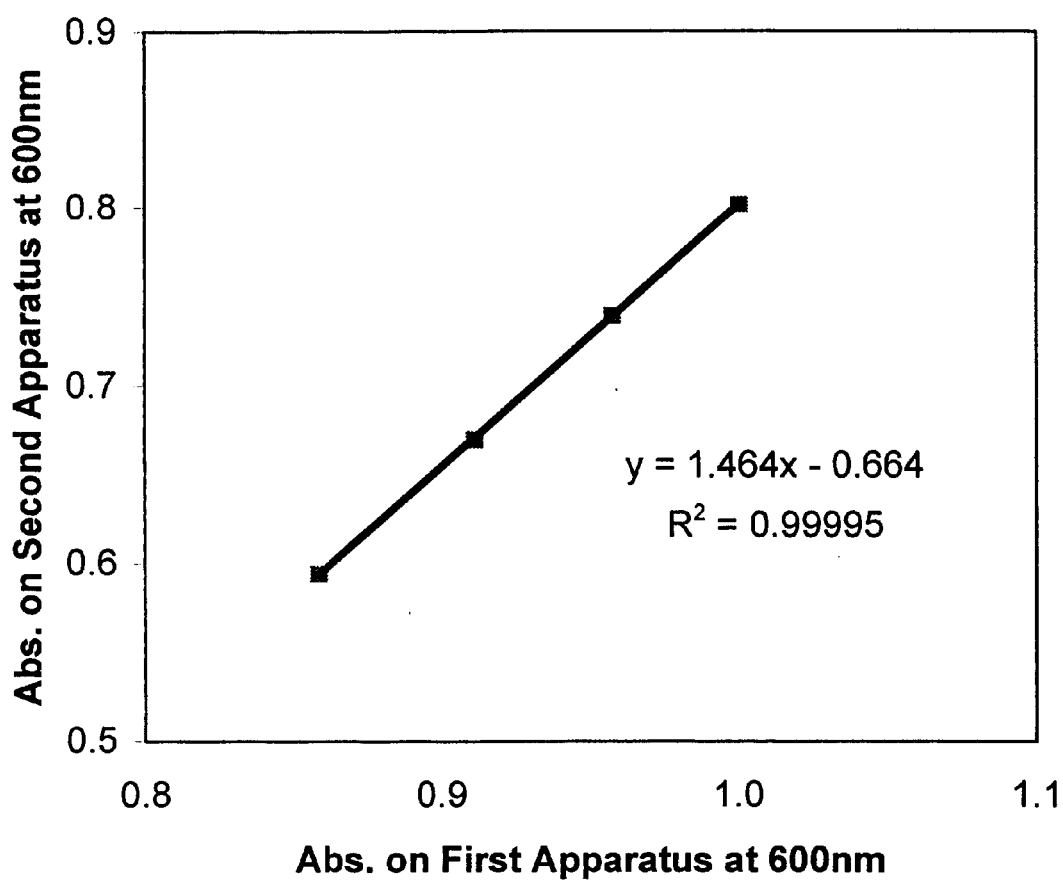
FIG. 5 is scatter plot of the absorbances of the four calibrators at 600 nm, when tested on the First Apparatus (x-axis) and the Second Apparatus (y-axis)
Figure 6:
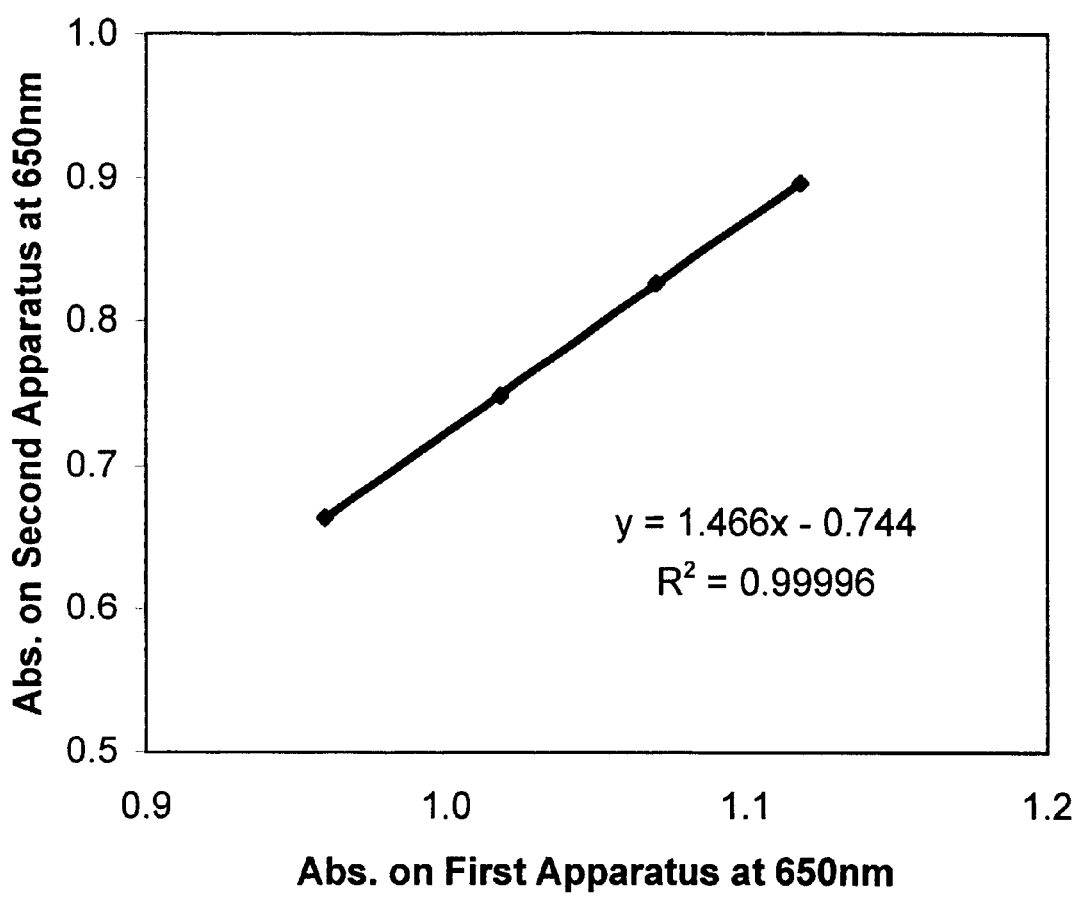
FIG. 6 is scatter plot of the absorbances of the four calibrators at 650 nm, when tested on the First Apparatus (x-axis) and the Second Apparatus (y-axis)
Figure 7:
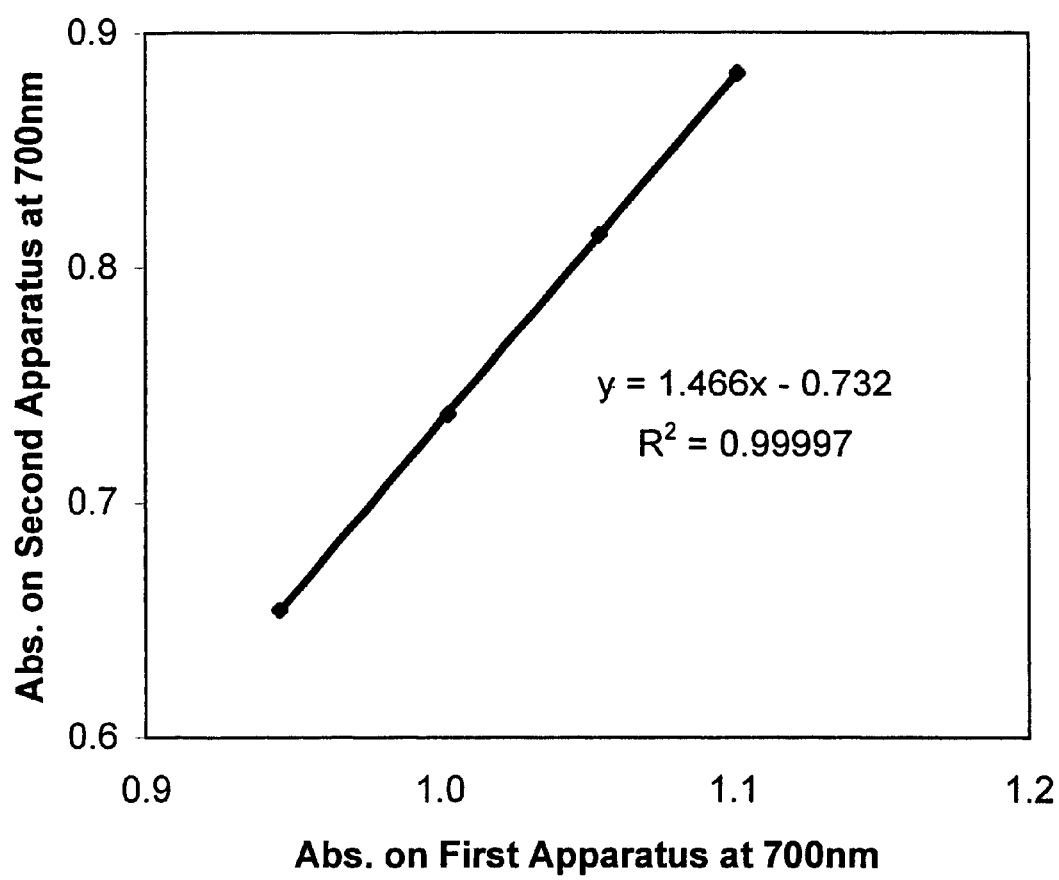
FIG. 7 is scatter plot of the absorbances of the four calibrators at 700 nm, when tested on the First Apparatus (x-axis) and the Second Apparatus (y-axis)
Figure 8:
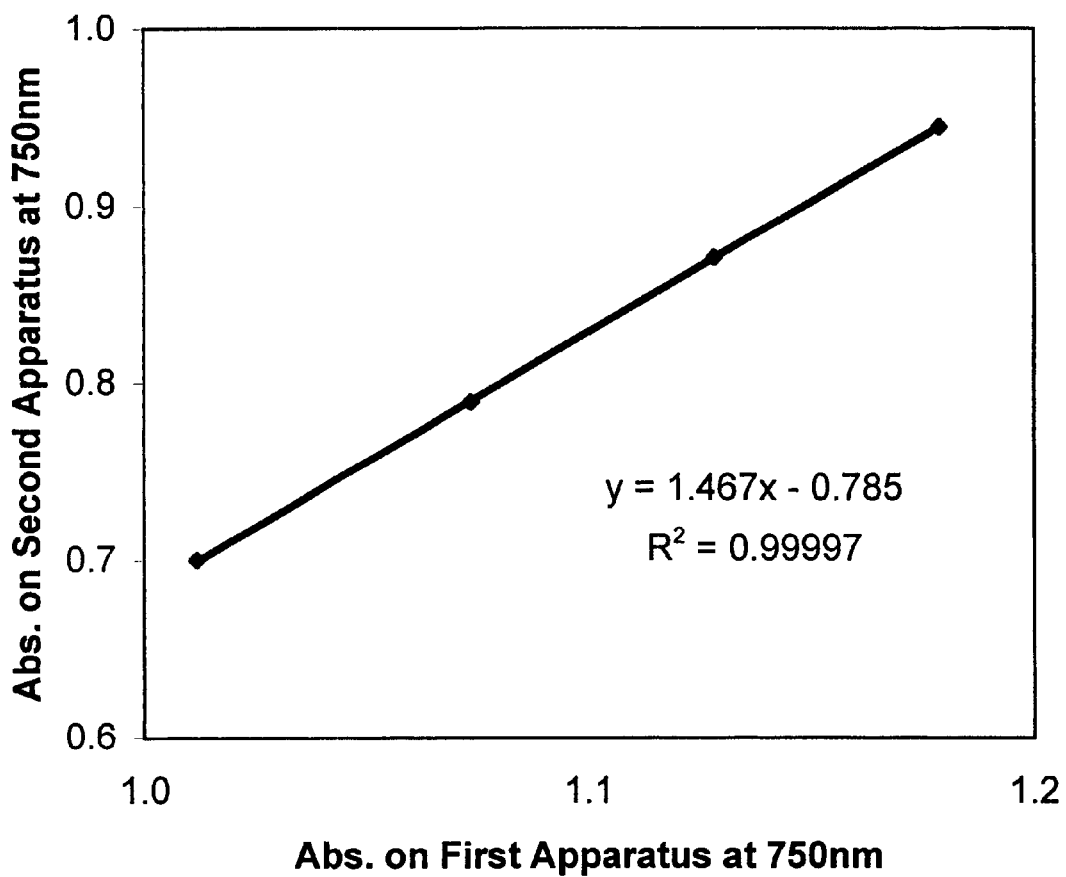
FIG. 8 is scatter plot of the absorbances of the four calibrators at 750 nm, when tested on the First Apparatus (x-axis) and the Second Apparatus (y-axis).

The absorbance spectra of four calibrators when tested on a "First Apparatus" are shown in FIG. 1; the absorbance spectra obtained from a "Second Apparatus" are shown in FIG. 2. The linear regression plots and equations for 500 nm, 550 nm, 600 nm, 650 nm, 700 nm and 750 nm are shown in FIGS. 3, 4, 5, 6, 7, and 8 respectively. Table 1 shows the y-intercepts and slopes for the wavelengths chosen as examples.

TABLE 1

| Wavelength (nm) | y-intercept | Slope | $R^2$ |
|---|---|---|---|
| 500 | −0.796 | 1.464 | 0.99995 |
| 550 | −0.801 | 1.465 | 0.99995 |
| 600 | −0.664 | 1.464 | 0.99995 |
| 650 | −0.744 | 1.466 | 0.99996 |
| 700 | −0.732 | 1.466 | 0.99997 |
| 750 | −0.785 | 1.467 | 0.99997 |

The slopes are very similar for the wavelength example shown in Table 1, but there are more significant differences for the y-intercepts. Theses numbers are very different from apparatus to apparatus. The large $R^2$ values (very close to 1) indicates the high correlation between the absorbances of the two apparatuses, and hence the reliability of the absorbance (or photometric) corrections—which is the basis for the recalibration process.

The y-intercepts and slopes in Table 1 were derived from the linear regression plots of absorbances for the calibrators obtained on the First Apparatus (x-axis) and Second Apparatus (y-axis).

The equation for wavelength 600 nm is y=1.464x−0.664, or in a more general form.

$Absorbance_{Second}$=1.464×$Absorbance_{First}$−0.664

Let us say that the absorbance for a particular sample at 600 nm on a Second Apparatus was 1.500. Before the Calibration algorithm from the First Apparatus (Primary Calibration Algorithm) for any analyte can be applied to the absorbances measured on Second Apparatus, the following adjustments must be made:

Adjusted absorbance = (Measured absorbance − {−0.664})/1.464

= (Measured absorbance + 0.664)/1.464

= (1.500 + 0.664)/1.464

= 1.478

Where −0.664 is a y-intercept and 1.464 is the slope from table above, for 600 nm. All wavelengths involved in the calibration algorithms must be adjusted similarly.

Quality control must be tested before and after calibrators are tested on the First Apparatus when preparing a Calibration Package, for assurance that the First Apparatus is performing precisely as it was when the calibrator algorithms were developed. In order for a Second Apparatus to use the Primary Calibration Algorithms derived for a First Apparatus, preferably the following two items are required:

1. A table like Table 1 which includes at least the wavelengths used, although all may be incorporated;
2. A series of calibrators or a calibration set.

While the present invention has been described with reference to what are presently considered to be preferred examples, it is to be understood that the invention is not limited to the disclosed examples. To the contrary, the invention is intended to cover various modifications and equivalents included within the spirit and scope of the appended claims.

I claim:

1. A method for transferring a calibration algorithm from a First Apparatus to a Second Apparatus comprising:
   (i) conducting a Primary Calibration of the First Apparatus to obtain at least one Primary Calibration Algorithm using a standard set of wavelengths;
   (ii) obtaining measurements of absorbance of a set of calibrators on the First Apparatus for at least one wavelength from the standard set of wavelengths;
   (iii) obtaining absorbance measurements of the set of calibrators on a Second Apparatus for at least one wavelength from the standard set of wavelengths;
   (iv) establishing a linear regression equation for at least one wavelength from the standard set of wavelengths using the absorbance measurements from the First Apparatus and the Second Apparatus; and
   (v) incorporating the at least one Primary Calibration Algorithm on the Second Apparatus.

2. A method of determining the concentration of an analyte in a sample in a Second Apparatus comprising:
   (i) transferring a calibration algorithm from a First Apparatus according to the method of claim 1;
   (ii) in the Second Apparatus measuring the absorbance of the sample for at least one wavelength from the standard set of wavelengths;
   (iii) adjusting the measurements of absorbance from the sample with the linear regression equation for each of the at least one wavelength to obtain a corrected absorbance; and
   (iv) calculating a concentration for the analyte using the corrected absorbance.

3. A method according to claim 2 wherein the Primary Calibration Algorithms and the calibration absorbance measurements on the First Apparatus are electronically stored and installed on the Second Apparatus.

4. A method according to claim 3 wherein the Primary Calibration Algorithms and the calibration absorbance measurements at the standard set of wavelengths on the First Apparatus are stored on a floppy diskette or an EPROM.

5. A method according to claim 2 wherein the samples used for the Primary Calibration are in a first type of vessel and the calibrators are in the same type of vessel.

6. A method according to claim 5 wherein the first type of vessel is a pipette tip, test tube (labelled or unlabelled), or blood bag tubing.

7. A method according to claim 6 wherein four calibrators are used.

8. A method according to claim 7 wherein the calibrators are all from the same batch.

9. A method according to claim 7 wherein the calibrators are exactly the same calibrators used to provide the absorbance measurement on the First Apparatus.

10. A method according to claim 8 wherein the calibrators mimic hemoglobin, bilirubin, turbidity or biliverdin.

11. A method according to claim 2 wherein the standard wavelengths are measured in the near infrared and adjacent visible light spectrum.

12. A method according to claim 11 wherein ten absorbance measurements are taken at each wavelength of the standard wavelength set.

13. A method for recalibrating a First Apparatus, a Second Apparatus, or both a First and Second Apparatus having a primary calibration algorithm comprising:
   i) incorporating in the First, Second, or both the First and the Second Apparatus absorbance measurements for at least one wavelength of a set of calibrators to produce incorporated calibrators absorbance measurements;
   (ii) obtaining measurements of absorbance of a similar set of calibrators on the First, Second, or both First and Second Apparatus for at least one wavelength from the standard set of wavelengths; and
   (iii) establishing a linear regression equation for at least one wavelength from the standard set of wavelengths using the incorporated calibrators absorbance measurements and the measurements of absorbance of the similar set of calibrators obtained on the First, Second, or both First and Second Apparatus.

14. A method of determining the concentration of an analyte in a sample in an apparatus recalibrated according to the method of claim 13, comprising:
   (i) measuring the absorbance of the sample in the recalibrated apparatus for at least one wavelength from the standard set of wavelengths;
   (ii) adjusting the measurements of absorbance from the sample with the linear regression equation for each of the at least one wavelength to obtain a corrected absorbance; and
   (iii) calculating a concentration for the analyte using the corrected absorbance.

15. A method according to claim 14 wherein the samples used for the Primary Calibration are in a first type of vessel and the calibrators are in the same type of vessel.

16. A method according to claim 15 wherein the first type of vessel is a pipette tip, test tube (labelled or unlabelled), or blood bag tubing.

17. A method according to claim 14 wherein four calibrators are used.

18. A method according to claim 17 wherein the calibrators are all from the same batch.

19. A method according to claim 18 wherein the calibrators mimic hemoglobin, bilirubin, turbidity or biliverdin.

20. A method according to claim 14 wherein the standard wavelengths are measured in the near infrared and adjacent visible light spectrum.

21. A method according to claim 20 wherein ten absorbance measurements are taken at each wavelength of the standard wavelength set.

22. A method of determining the concentration of an interferent in a sample in a Second Apparatus using a calibration algorithm from a First Apparatus comprising:
   (i) conducting a Primary Calibration of the First Apparatus to obtain at least one Primary Calibration Algorithm using a standard set of wavelengths in the near infrared and adjacent visible range and storing the at least one Primary Calibration Algorithm in a calibration information package;

(ii) obtaining calibrators' absorbance measurements of a set of calibrators for at least one wavelength from the standard set of wavelengths on said First Apparatus and storing the calibrators' absorbance measurements in a calibration information package;

(iii) installing the calibrators' absorbance measurements and the at least one Primary Calibration Algorithms stored in a calibration information package in the Second Apparatus;

(iv) obtaining measurements of absorbance of the set of calibrators on a Second Apparatus for at least one wavelength from the standard set of wavelengths;

(v) establishing a linear regression equation for each of the at least one wavelength from the standard set of wavelengths using the calibration absorbance measurements from the First Apparatus and the measurements of absorbance from the Second Apparatus and electronically storing the linear regression equation in the Second Apparatus;

(vi) measuring the absorbance of the sample for at least one wavelengths from the standard set of wavelengths in the Second Apparatus;

(vii) adjusting the measurements of absorbance from the sample with the First linear regression equation for each of the at least one wavelength to obtain a corrected absorbance; and (viii) calculating a concentration for the analyte using the corrected absorbance.

23. A method of determining the concentration of an analyte in a sample in a Second Apparatus comprising:

(i) conducting a Primary Calibration of a First Apparatus to obtain at least one Primary Calibration Algorithm using a standard set of wavelengths, and incorporating the at least one Primary Calibration Algorithm on the Second Apparatus;

(ii) measuring the absorbance of the sample for at least two wavelengths from the standard set of wavelengths in the Second Apparatus;

(iii) obtaining a mathematical derivative of the measured absorbance from step (ii); and (iv) calculating a concentration for the analyte using the derivative of absorbance measurement.

24. A method according to claim 23 wherein the derivative of the measured absorbance is chosen from at least one of the first, second, or third derivatives.

* * * * *